(12) United States Patent
Schädler et al.

(10) Patent No.: US 8,206,957 B2
(45) Date of Patent: *Jun. 26, 2012

(54) PROCESS FOR THE ENZYMATIC PREPARATION OF CITRONELLAL

(75) Inventors: Andreas Schädler, Weyher (DE); Thomas Friedrich, Darmstadt (DE); Rainer Stürmer, Rödersheim-Gronau (DE); Sabine Rinck, Heidelberg (DE)

(73) Assignee: BASF SE, Ludwigshafen (DE)

( * ) Notice: Subject to any disclaimer, the term of this patent is extended or adjusted under 35 U.S.C. 154(b) by 1004 days.

This patent is subject to a terminal disclaimer.

(21) Appl. No.: 12/159,531

(22) PCT Filed: Dec. 19, 2006

(86) PCT No.: PCT/EP2006/069894
§ 371 (c)(1),
(2), (4) Date: Jun. 27, 2008

(87) PCT Pub. No.: WO2007/077121
PCT Pub. Date: Jul. 12, 2007

(65) Prior Publication Data
US 2008/0293111 A1 Nov. 27, 2008

(30) Foreign Application Priority Data
Dec. 30, 2005 (DE) .......................... 10 2005 063 191

(51) Int. Cl.
*C12P 7/24* (2006.01)
(52) U.S. Cl. ...... 435/147; 435/132; 435/189; 435/255.2
(58) Field of Classification Search .................. 435/132, 435/147, 189, 255.2
See application file for complete search history.

(56) References Cited

U.S. PATENT DOCUMENTS
2005/0148057 A1* 7/2005 Kimoto et al. ................ 435/189

FOREIGN PATENT DOCUMENTS
DE 10019377 A1 10/2001
EP 1557459 A1 7/2005

OTHER PUBLICATIONS

Niino et al. J. Biol. Chem. (1995) 270(5): 1983-1991.*
Brown et al. J. Biol.Chem. (1998) 273(49): 32753-32762.*
Hall, M., et al., "Asymmetric Whole-Cell Bioreduction of an α,β-Unsaturated Aldehyde (Citral): Competing *Prim*-Alcohol Dehydrogenase and C-C Lyase Activities", Tetrahedron: Asymmetry, 2006, vol. 17, pp. 3058-3062.
Müller, A., et al., "Enzymatic Reduction of the α,β-Unsaturated Carbon Bond in Citral", Journal of Molecular Catalysis B: Enzymatic, 2006, vol. 38, pp. 126-130.
Williams, R. E., at al., "New Used for an Old Enzyme—the Old Yellow Enzyme Family of Flavoenzymes", Microbiology, 2002, vol. 148, pp. 1607-1614.

* cited by examiner

*Primary Examiner* — Susan Hanley
(74) *Attorney, Agent, or Firm* — Connolly Bove Lodge & Hutz LLP

(57) ABSTRACT

A process for preparing optically active saturated aldehydes or alcohols of the formula (2) from α,β-unsaturated aldehydes of the formula (1) by reduction in the presence of an enoate reductase
(i) having the polypeptide sequence SEQ ID No. 1 or 2, or
(ii) having a polypeptide sequence which is at least 80% identical to the sequence of SEQ ID No. 1 or 2.

9 Claims, No Drawings

SEQUENCE LISTING

```
<160> NUMBER OF SEQ ID NOS: 2

<210> SEQ ID NO 1
<211> LENGTH: 400
<212> TYPE: PRT
<213> ORGANISM: Saccharomyces cerevisiae

<400> SEQUENCE: 1

Met Pro Phe Val Lys Asp Phe Lys Pro Gln Ala Leu Gly Asp Thr Asn
1               5                   10                  15

Leu Phe Lys Pro Ile Lys Ile Gly Asn Asn Glu Leu Leu His Arg Ala
            20                  25                  30

Val Ile Pro Pro Leu Thr Arg Met Arg Ala Gln His Pro Gly Asn Ile
        35                  40                  45

Pro Asn Arg Asp Trp Ala Val Glu Tyr Tyr Ala Gln Arg Ala Gln Arg
    50                  55                  60

Pro Gly Thr Leu Ile Ile Thr Glu Gly Thr Phe Pro Ser Pro Gln Ser
65                  70                  75                  80
```

-continued

```
Gly Gly Tyr Asp Asn Ala Pro Gly Ile Trp Ser Glu Gln Ile Lys
                85                  90                  95

Glu Trp Thr Lys Ile Phe Lys Ala Ile His Glu Asn Lys Ser Phe Ala
        100                 105                 110

Trp Val Gln Leu Trp Val Leu Gly Trp Ala Ala Phe Pro Asp Thr Leu
            115                 120                 125

Ala Arg Asp Gly Leu Arg Tyr Asp Ser Ala Ser Asp Asn Val Tyr Met
    130                 135                 140

Asn Ala Glu Gln Glu Glu Lys Ala Lys Lys Ala Asn Asn Pro Gln His
145                 150                 155                 160

Ser Ile Thr Lys Asp Glu Ile Lys Gln Tyr Val Lys Glu Tyr Val Gln
                165                 170                 175

Ala Ala Lys Asn Ser Ile Ala Ala Gly Ala Asp Gly Val Glu Ile His
            180                 185                 190

Ser Ala Asn Gly Tyr Leu Leu Asn Gln Phe Leu Asp Pro His Ser Asn
        195                 200                 205

Asn Arg Thr Asp Glu Tyr Gly Gly Ser Ile Glu Asn Arg Ala Arg Phe
    210                 215                 220

Thr Leu Glu Val Val Asp Ala Val Val Asp Ala Ile Gly Pro Glu Lys
225                 230                 235                 240

Val Gly Leu Arg Leu Ser Pro Tyr Gly Val Phe Asn Ser Met Ser Gly
                245                 250                 255

Gly Ala Glu Thr Gly Ile Val Ala Gln Tyr Ala Tyr Val Leu Gly Glu
            260                 265                 270

Leu Glu Arg Arg Ala Lys Ala Gly Lys Arg Leu Ala Phe Val His Leu
        275                 280                 285

Val Glu Pro Arg Val Thr Asn Pro Phe Leu Thr Glu Gly Glu Gly Glu
    290                 295                 300

Tyr Asn Gly Gly Ser Asn Lys Phe Ala Tyr Ser Ile Trp Lys Gly Pro
305                 310                 315                 320

Ile Ile Arg Ala Gly Asn Phe Ala Leu His Pro Glu Val Val Arg Glu
                325                 330                 335

Glu Val Lys Asp Pro Arg Thr Leu Ile Gly Tyr Gly Arg Phe Phe Ile
            340                 345                 350

Ser Asn Pro Asp Leu Val Asp Arg Leu Glu Lys Gly Leu Pro Leu Asn
        355                 360                 365

Lys Tyr Asp Arg Asp Thr Phe Tyr Lys Met Ser Ala Glu Gly Tyr Ile
    370                 375                 380

Asp Tyr Pro Thr Tyr Glu Glu Ala Leu Lys Leu Gly Trp Asp Lys Asn
385                 390                 395                 400

<210> SEQ ID NO 2
<211> LENGTH: 400
<212> TYPE: PRT
<213> ORGANISM: Saccharomyces cerevisiae

<400> SEQUENCE: 2

Met Pro Phe Val Lys Gly Phe Glu Pro Ile Ser Leu Arg Asp Thr Asn
1               5                   10                  15

Leu Phe Glu Pro Ile Lys Ile Gly Asn Thr Gln Leu Ala His Arg Ala
            20                  25                  30

Val Met Pro Pro Leu Thr Arg Met Arg Ala Thr His Pro Gly Asn Ile
        35                  40                  45

Pro Asn Lys Glu Trp Ala Ala Val Tyr Tyr Gly Gln Arg Ala Gln Arg
    50                  55                  60
```

```
Pro Gly Thr Met Ile Ile Thr Glu Gly Thr Phe Ile Ser Pro Gln Ala
 65                  70                  75                  80

Gly Gly Tyr Asp Asn Ala Pro Gly Ile Trp Ser Asp Glu Gln Val Ala
                 85                  90                  95

Glu Trp Lys Asn Ile Phe Leu Ala Ile His Asp Cys Gln Ser Phe Ala
                100                 105                 110

Trp Val Gln Leu Trp Ser Leu Gly Trp Ala Ser Phe Pro Asp Val Leu
            115                 120                 125

Ala Arg Asp Gly Leu Arg Tyr Asp Cys Ala Ser Asp Arg Val Tyr Met
130                 135                 140

Asn Ala Thr Leu Gln Glu Lys Ala Lys Asp Ala Asn Asn Leu Glu His
145                 150                 155                 160

Ser Leu Thr Lys Asp Asp Ile Lys Gln Tyr Ile Lys Asp Tyr Ile His
                165                 170                 175

Ala Ala Lys Asn Ser Ile Ala Ala Gly Ala Asp Gly Val Glu Ile His
                180                 185                 190

Ser Ala Asn Gly Tyr Leu Leu Asn Gln Phe Leu Asp Pro His Ser Asn
            195                 200                 205

Lys Arg Thr Asp Glu Tyr Gly Gly Thr Ile Glu Asn Arg Ala Arg Phe
            210                 215                 220

Thr Leu Glu Val Val Asp Ala Leu Ile Glu Thr Ile Gly Pro Glu Arg
225                 230                 235                 240

Val Gly Leu Arg Leu Ser Pro Tyr Gly Thr Phe Asn Ser Met Ser Gly
                245                 250                 255

Gly Ala Glu Pro Gly Ile Ile Ala Gln Tyr Ser Tyr Val Leu Gly Glu
                260                 265                 270

Leu Glu Lys Arg Ala Lys Ala Gly Lys Arg Leu Ala Phe Val His Leu
            275                 280                 285

Val Glu Pro Arg Val Thr Asp Pro Ser Leu Val Glu Gly Glu Gly Glu
            290                 295                 300

Tyr Ser Glu Gly Thr Asn Asp Phe Ala Tyr Ser Ile Trp Lys Gly Pro
305                 310                 315                 320

Ile Ile Arg Ala Gly Asn Tyr Ala Leu His Pro Glu Val Val Arg Glu
                325                 330                 335

Gln Val Lys Asp Pro Arg Thr Leu Ile Gly Tyr Gly Arg Phe Phe Ile
                340                 345                 350

Ser Asn Pro Asp Leu Val Tyr Arg Leu Glu Glu Gly Leu Pro Leu Asn
            355                 360                 365

Lys Tyr Asp Arg Ser Thr Phe Tyr Thr Met Ser Ala Glu Gly Tyr Thr
            370                 375                 380

Asp Tyr Pro Thr Tyr Glu Glu Ala Val Asp Leu Gly Trp Asn Lys Asn
385                 390                 395                 400
```

PROCESS FOR THE ENZYMATIC PREPARATION OF CITRONELLAL

RELATED APPLICATIONS

This application is a national stage application (under 35 U.S.C. §371) of PCT/EP2006/069894, filed Dec. 19, 2006, which claims benefit of German application 10 2005 063 191.6, filed Dec. 30, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is SequenceListing__12810__00705_US. The size of the text file is 7.19 KB, and the text file was created on Jun. 27, 2008.

The invention relates to an enzymatic process for preparing optically active saturated aldehydes or alcohols of the formula from α,β-unsaturated aldehydes, in particular to a process for preparing citronellal.

BACKGROUND OF THE INVENTION (R)-(+) Citronellal is an important chemical intermediate which is used in the preparation of menthol, for example.

The chemical methods of preparing (R)-(+)citronellal, starting from citral, require very complicated methods (exclusion of oxygen and water) which result in high costs for an industrial synthesis.

OBJECT OF THE INVENTION

It was the object to provide a process for preparing citronella by enantioselective reduction of citral, which process delivers a high chemical yield of citronellal with maximum enantiomeric purity.

DESCRIPTION OF THE INVENTION

The present invention relates to a process for preparing optically active saturated aldehydes or alcohols of the formula (2) from α,β-unsaturated aldehydes of the formula (1) by reduction in the presence of an enoate reductase
(i) having the polypeptide sequence SEQ ID No. 1 or 2, or
(ii) having a polypeptide sequence which is at least 80% identical to the sequence of SEQ ID No. 1 or 2,

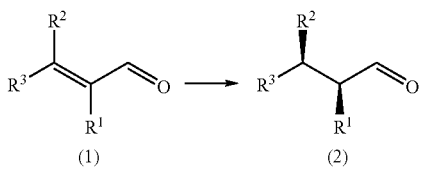

in which R1 and R2 independently of one another are H, $C_1$-$C_4$-alkyl, R3 is H, $C_1$-$C_{10}$-alkyl or alkenyl, in branched and unbranched form.

The process of the invention may be carried out using α,β-unsaturated aldehydes of the formula (1) in which R1 and R2 independently of one another are H, $C_1$-$C_4$-alkyl in branched and unbranched forms, R3 is H, $C_1$-$C_6$-alkyl or alkenyl in branched and unbranched forms. The alkyl and alkenyl radicals may also be mono- or polysubstituted.

Particularly suitable substrates for the process of the invention are those α,β-unsaturated aldehydes of the formula (1) in which R1 is H, R2 is $CH_3$ and R3 is —$CH_2$—$CH_2$—CH= $(CH_3)_2$ (citral in the cis or the trans form), and those in which R1 is $CH_3$, R2 is H and R3 is $CH_3$ (2-methyl-pent-2-en-1-al).

The enoate reductases used according to the invention, occasionally and to some extent, also reduce, in addition to the double bond in the apposition to the carbonyl function, said carbonyl function itself, producing in this case the corresponding alcohol.

Enoate reductases which are suitable for the process of the invention are those enzymes which are capable of reducing 2-methyl-pent-2-en-1-al in an NADPH-dependent reaction to give (S)-2-methyl-pentan-1-al. This reaction is also referred to as model reaction hereinbelow.

Furthermore, the enoate reductases suitable for the process of the invention possess a polypeptide sequence according to SEQ ID No. 1 or No. 2 or a polypeptide sequence which is at least 80%, preferably at least 90%, particularly preferably at least 95% and in particular at least 97%, 98% or 99%, identical to the sequence of SEQ ID No. 1 or 2.

A polypeptide with SEQ ID No. 1 is the OYE2 gene from baker's yeast (*Saccharomyces cerevisiae* gene locus YHR179W).

A polypeptide with SEQ ID No. 2 is the OYE3 gene from baker's yeast (Saccharomyces cerevisiae gene locus YPL171C).

For the purposes described herein, the sequence identity is to be determined by the "GAP" computer program of the Genetics Computer Group (GCG) of the University of Wisconsin, it being intended to employ Version 10.3 using the standard parameters recommended by GCG.

Starting from SEQ ID No. 1 or 2, such enoate reductases may be obtained by specific or randomized mutagenesis processes known to the skilled worker. Alternatively, however, it is also possible to screen microorganisms, preferably those of the genera *Alishewanella, Alterococcus, Aquamonas, Aranicola, Arsenophonus, Azotivirga, Brenneria, Buchnera* (aphid P-endosymbionts), *Budvicia, Buttiauxella, Candidatus Phlomobacter, Cedecea, Citrobacter, Dickeya, Edwardsiella, Enterobacter, Erwinia, Escherichia, Ewingella, Grimontella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Sodalis, Tatumella, Trabulsiella, Wigglesworthia, Xenorhabdus, Yersinia* and *Yokenella*, for enoate reductases which catalyze the above-mentioned model reaction and whose amino acid sequence already has the required sequence identity to SEQ ID No. 1 or 2 or is obtained via mutagenesis processes.

The enoate reductase may be used in a purified or partially purified form or else in the form of the microorganism itself. Processes for recovering and purifying dehydrogenases from microorganisms are sufficiently known to the skilled worker.

The enantioselective reduction with said enoate reductase is preferably carried out in the presence of a suitable cofactor (also referred to as cosubstrate). Cofactors commonly used for reducing the ketone are NADH and/or NADPH. In addition, it is possible to employ enoate reductases as cellular systems that inherently comprise cofactor or to add alternative redox mediators (A. Schmidt, F. Hollmann and B. Bühler "Oxidation of Alcohols" in K. Drauz und H. Waldmann, Enzyme Catalysis in Organic Synthesis 2002, Vol. III, 991-1032, Wiley-VCH, Weinheim).

Preference is moreover given to carrying out the enantioselective reduction with said enoate reductase in the presence of a suitable reducing agent which regenerates the cofactor oxidized in the course of said reduction. Examples of suitable reducing agents are sugars, in particular hexoses, such as glucose, mannose, fructose, and/or oxidizable alcohols, in particular ethanol, propanol or isopropanol, and also formate, phosphite or molecular hydrogen. In order to oxidize the reducing agent and, connected therewith, to regenerate the coenzyme, a second dehydrogenase may be added, such as, for example, glucose dehydrogenase, if the reducing agent used is glucose, or formate dehydrogenase, if the reducing agent used is formate. Said second dehydrogenase may be used as free or immobilized enzyme or in the form of free or immobilized cells. Its preparation may be carried out both separately and by way of coexpression in a (recombinant) reductase strain.

A preferred embodiment of the claimed process is to regenerate the cofactors by an enzymatic system in which a second dehydrogenase, particularly preferably a glucose dehydrogenase, is used.

The invention further relates to the use of enoate reductase for preparing citronellal.

The preferred cofactors used in this embodiment are $NAD^+$ and $NADP^+$, respectively, which may be regenerated again with appropriate cosubstrates (oxidizing agents). The preferred cosubstrate which may be used here is acetone which, together with the ADH already present and/or an additionally employed dehydrogenase, regenerates the cofactor and is reduced to isopropanol in the process.

"Enantioselectivity" means for the purposes of the present invention that the enantiomer excess, ee (in %), of the S-enantiomer, which is calculated in the known manner according to:

$$ee(\%)=S\text{-enantiomer}-R\text{-enantiomer}/(S\text{-enantiomer}-R\text{-enantiomer})\times 100,$$

is at least 80%, preferably at least 90%, in particular at least 95% and especially at least 97%.

The enoate reductases used according to the invention may be employed in a free or immobilized form. An immobilized enzyme means an enzyme which is fixed to an inert support. Suitable support materials and the enzymes immobilized thereon are disclosed in EP-A-1149849, EP-A-1 069 183 and DE-A 100193773 and in the references cited therein. On this matter, reference is made to the disclosure of these publications in their entirety. Examples of suitable support materials are clays, clay minerals such as kaolinite, diatomaceous earth, perlite, silicon dioxide, aluminum oxide, sodium carbonate, calcium carbonate, cellulose powder, anion exchanger materials, synthetic polymers such as polystyrene, acrylic resins, phenol-formaldehyde resins, polyurethanes and polyolefins such as polyethylene and polypropylene. The support materials are usually employed in a finely divided, particulate form for preparing the supported enzymes, with preference being given to porous forms. The particle size of the support material is usually no more than 5 mm, in particular no more than 2 mm (sieve grade). Analogously, when using the dehydrogenase as whole cell catalyst, a free or immobilized form may be chosen. Examples of support materials are calcium alginate and carrageenan. Enzymes as well as cells may also be crosslinked directly with glutaraldehyde (crosslinking to give CLEAs). Corresponding and other immobilization processes are described, for example, in J. Lalonde and A. Margolin "Immobilization of Enzymes" in K. Drauz and H. Waidmann, Enzyme Catalysis in Organic Synthesis 2002, Vol. III, 991-1032, Wiley-VCH, Weinheim.

The reaction may be carried out in aqueous or nonaqueous reaction media or in 2-phase systems or (micro)emulsions.

The aqueous reaction media are preferably buffered solutions which usually have a pH of from 4 to 8, preferably from 5 to 8. The aqueous solvent may, in addition to water, also comprise at least one alcohol, for example ethanol or isopropanol or dimethyl sulfoxide.

Nonaqueous reaction media mean reaction media which comprise less than 1% by weight, preferably less than 0.5% by weight, water, based on the total mass of the reaction medium. The reaction is preferably carried out in an organic solvent.

Examples of suitable solvents are aliphatic hydrocarbons, preferably having from 5 to 8 carbon atoms, such as pentane, cyclopentane, hexane, cyclohexane, heptane, octane or cyclooctane, halogenated aliphatic hydrocarbons, preferably having one or two carbon atoms, such as dichloromethane, chloroform, carbon tetrachloride, dichloroethane or tetrachloroethane, aromatic hydrocarbons such as benzene, toluene, the xylenes, chlorobenzene or dichlorobenzene, aliphatic acyclic and cyclic ethers or alcohols, preferably having from 4 to 8 carbon atoms, such as diethyl ether, methyl tert-butyl ether, ethyl tert-butyl ether, dipropyl ether, diisopropyl ether, dibutyl ether, tetrahydrofuran or esters such as ethyl acetate or n-butyl acetate or ketones such as methyl isobutyl ketone or dioxane or mixtures thereof, Particular preference is given to using the above-mentioned ethers, in particular tetrahydrofuran.

The reduction with enoate reductase is preferably carried out in an aqueous-organic, in particular aqueous, reaction medium.

Substrate (1) is used in the enzymic reduction preferably at a concentration of from 0.1 g/l to 500 g/l, particularly preferably from 1 g/l to 50 g/l, and may subsequently be fed in continuously or batchwise.

The enzymic reduction is usually carried out at a reaction temperature below the deactivation temperature of the reductase used and above −10° C. Said temperature is particularly preferably in the range from 0 to 100° C., in particular from 15 to 60° C. and especially from 20 to 40° C., for example at about 30° C.

The procedure may involve, for example, initially introducing substrate (1) with the enoate reductase, the solvent and, if appropriate, the coenzymes, if appropriate with a second dehydrogenase for regenerating the coenzyme, and/or further reducing agents and mixing the mixture, for example by stirring or shaking. However, it is also possible to immobilize the reductase in a reactor for example in a column and to conduct a mixture comprising the substrate and, if appropriate, coenzymes and/or cosubstrates through the reactor. To this end, the mixture may be circulated through the reactor, until the desired conversion has been achieved.

In the process, the double bond in the $\alpha,\beta$ position to the carbonyl function is reduced to a single bond; occasionally, the carbonyl function itself is reduced to the alcohol function. The reduction is usually carried out to a conversion of at least 70%, particularly preferably of at least 85% and in particular of at least 95%, based on the substrate present in the mixture. The progress of the reaction, i.e. the sequential reduction of the double bond, may be monitored here by customary methods such as gas chromatography or high pressure liquid chromatography.

"Functional equivalents" or analogs of the specifically disclosed enzymes are, for the purposes of the present invention, polypeptides which differ therefrom and which furthermore possess the desired biological activity such as, for example, substrate specificity. Thus, for example, "functional equivalents" mean enzymes which catalyze the model reaction and which have at least 20%, preferably 50%, particularly preferably 75%, very particularly preferably 90%, of the activity of an enzyme comprising any of the amino acid sequences listed under SEQ ID No. 1 or 2. Moreover, functional equivalents are preferably stable between pH 4 to 10 and advantageously possess a pH optimum between pH 5 and 8 and a temperature optimum in the range from 20° C. to 80° C.

"Functional equivalents" mean, according to the invention, in particular also mutants which have in at least one sequence position of the abovementioned amino acid sequences an amino acid other than the specifically mentioned one but which nevertheless possess one of the abovementioned biological activities. "Functional equivalents" thus comprise the mutants obtainable by one or more amino acid additions, substitutions, deletions and/or inversions, it being possible for said modifications to occur in any sequence position, as long as they result in a mutant having the property profile of the invention. Functional equivalence in particular also exists, if the reactivity patterns between the mutant and the unmodified polypeptide correspond qualitatively, i.e., for example, the same substrates are reacted at different rates.

Examples of suitable amino acid substitutions can be found in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and also "functional derivatives".

In this context, "precursors" are natural or synthetic precursors of the polypeptides with or without the desired biological activity.

"Functional derivatives" of polypeptides of the invention may likewise be prepared with the aid of known techniques at functional amino acid side groups or at their N-terminal or C-terminal ends. Derivatives of this kind comprise, for example, aliphatic esters of carboxylic acid groups, amides of carboxylic acid groups, which amides are obtainable by reacting with ammonia or with a primary or secondary amine; N-acyl derivatives of free amino groups, which derivatives are prepared by reacting with acyl groups; or O-acyl derivatives of free hydroxyl groups, which derivatives are prepared by reacting with acyl groups.

In the case of a possible protein glycosylation, "functional equivalents" of the invention comprise proteins of the above-described type in deglycosylated or glycosylated form and also modified forms which can be obtained by altering the glycosylation pattern.

"Functional equivalents" naturally also comprise polypeptides which are available from other organisms and also naturally occurring variants. For example, areas of homologous sequence regions can be established by sequence comparison and equivalent enzymes can be determined on the basis of the specific guidelines of the invention.

"Functional equivalents" likewise comprise fragments, preferably individual domains or sequence motifs, of the polypeptides of the invention, which fragments have, for example, the desired biological function.

"Functional equivalents" are moreover fusion proteins which contain any of the above-mentioned polypeptide sequences or functional equivalents derived therefrom and at least one further heterologous sequence which is functionally different therefrom and is functionally linked N-terminally or C-terminally (i.e. without any substantial reciprocal functional impairment of the fusion protein moieties). Nonlimiting examples of such heterologous sequences are signal peptides or enzymes, for example.

Homologs of the proteins of the invention may be identified by screening combinatorial libraries of mutants such as truncation mutants, for example. For example, a variegated library of protein variants may be generated by combinatorial mutagenesis at the nucleic acid level, for example by enzymically ligating a mixture of synthetic oligonucleotides. There are a large number of methods which may be used for preparing libraries of potential homologs from a degenerate oligonucleotide sequence. A degenerate gene sequence may be synthesized chemically in a DNA synthesizer and the synthetic gene may then be ligated into a suitable expression vector. Using a degenerate set of genes makes it possible to provide all the sequences in a mixture which encode the desired set of potential protein sequences. Processes for synthesizing degenerate oligonucleotides are known to the skilled worker (e.g. Narang, S. A. (1983) Tetrahedron 39.3; Itakura et al. (1984) Annu. Rev, Biochem. 53:323; Itakura et al., (1984) Science 198:1056; Ike et al. (1983) Nucleic Acids Res. 11:477).

A plurality of techniques for screening gene products of combinatorial libraries which have been prepared by point mutations or truncation and for screening cDNA libraries for gene products having a selected property are known in the prior art. These techniques can be adapted for rapidly screening the gene libraries which have been generated by combinatorial mutagenesis of homologs of the invention. The most frequently employed techniques for screening large gene libraries which are subject to high-throughput analysis comprise cloning the gene library into replicable expression vectors, transforming the appropriate cells with the resulting vector library and expressing the combinatorial genes under conditions under which detection of the desired activity facilitates isolation of the vector which encodes the gene whose product was detected. Recursive ensemble mutagenesis (REM), a technique which increases the frequency of functional mutants in the libraries, may be used in combination with the screening tests in order to identify homologs (Arkin and Yourvan (1992) PNAS 89:7811-7815; Delgrave et al. (1993) Protein Engineering 6(3):327-331).

The invention relates furthermore to nucleic acid sequences (single- and double-stranded DNA and RNA sequences, such as cDNA and mRNA, for example) which code for an enzyme with reductase activity of the invention. Preference is given to nucleic acid sequences which code, for example, for amino acid sequences according to SEQ ID No. 1 or 2 or for characteristic partial sequences thereof.

All of the nucleic acid sequences mentioned herein can be prepared in a manner known per se by chemical synthesis from the nucleotide building blocks, for example by means of fragment condensation of individual overlapping, complementary nucleic acid building blocks of the double helix. Oligonucleotides may, for example, be synthesized chemically, in a known manner, using the phosphoamidite method (Voet, Voet, 2nd edition, Wiley Press New York, pages 896-897). The assembly of synthetic oligonucleotides and filling-in of gaps with the aid of the DNA polymerase Klenow fragment and ligation reactions and also general cloning methods are described in Sambrook et al. (1989), Molecular Cloning: A laboratory manual, Cold Spring Harbor Laboratory Press.

Further Embodiments for Carrying Out the Enzymic Reduction Process of the Invention The enoate reductases may be used as free or immobilized enzyme in the process of the invention.

The process of the invention is advantageously carried out at a temperature between 0° C. to 95° C., preferably between 10° C. to 85° C., particularly preferably between 15° C. to 75° C.

In the process of the invention, the pH is advantageously kept between pH 4 and 12, preferably between pH 4.5 and 9, particularly preferably between pH 5 and 8.

In the process of the invention, enantiomerically pure or chiral products (2) mean enantiomers which exhibit enantiomer enrichment. Enantiomeric purities of at least 70% ee, preferably of at least 80% ee, particularly preferably of at least 90% ee, very particularly preferably of at least 98% ee, are preferably achieved in the process.

It is possible to use for the process of the invention growing cells which comprise the nucleic acids, nucleic acid constructs or vectors of the invention. It is also possible to use resting or disrupted cells. Disrupted cells mean, for example, cells which have been made permeable by way of treatment with solvents, for example, or cells which have been broken up by way of treatment with enzymes, by way of mechanical treatment (e.g. French press or ultrasonication) or by way of another method. The crude extracts obtained in this manner are advantageously suitable for the process of the invention. It is also possible to use purified or partially purified enzymes for the process. Immobilized microorganisms or enzymes which may advantageously be applied in the reaction are likewise suitable.

The process of the invention can be operated batchwise, semi-batchwise or continuously.

The process may advantageously be carried out in bioreactors as described, for example, in Biotechnology, volume 3, 2nd edition, Rehm et al. Eds., (1993), in particular chapter II.

The examples below are intended to illustrate but not to limit the invention. In this context, reference is made to the accompanying figures in which:

EXPERIMENTAL SECTION

Biotransformation of 2-methyl-pent-2-en-1-al with *Saccharomyces cerevisiae*

Biotransformations were carried out in 500 ml Erlenmeyer flasks with baffles. Said flasks were charged in each case with 126 ml of transformation solution. To these, in each case 21 g of D-glucose were added. The desired pH (between 6 and 8.5) was adjusted. The amount of substrate per flask was 200 mg of 2-methylpent-2-en-1-al. The experiment was started by adding 21 g of baker's yeast, and the reaction mixtures were placed in an incubator at the desired temperature (between 28 and 37° C.) (agitated at 240 rpm). Samples were taken after 6, 12, 18, 24, 36, 48 hours and analyzed by gas chromatography.

The highest conversion rates (40-70%) were achieved between pH 7.5 and pH 8.5. The optical purity at pH=8.5 and T=37° C. was ee=92.1 with a conversion of 66.6%.

Biotransformation of Citral with *Saccharomyces cerevisiae*

Biotransformations were carried out in 500 ml Erlenmeyer flasks with baffles. Said flasks were charged in each case with 126 ml of transformation solution. To these, in each case 21 g of D-glucose were added. The desired pH (between 6 and 8.5) was adjusted. The amount of substrate per flask was 210 mg of citral (citral was a 70:30 cis/trans mixture). The experiment was started by adding 21 g of baker's yeast, and the reaction mixtures were placed in an incubator at the desired temperature (between 28 and 37° C.) (agitated at 240 rpm). Samples were taken after 6, 12, 18, 24, 36, 48 hours and analyzed by gas chromatography.

In addition to (R)-(+)citronellal, (R)-(+)-β-citronellol as well as nerol and geraniol were also obtained.

Transformation Solution 53.4 g of $Na_2HPO_4$ and 21 g of D-glucose and 126 ml of distilled water (pH adjusted to between 6 and 8.5).

What is claimed is:

1. A process for preparing an optically active aldehyde and/or a corresponding alcohol of formula (2) comprising reducing α,β-unsaturated aldehyde of formula (1) in the presence of an enoate reductase
   (i) having the amino acid sequence SEQ ID No. 1 or 2; or
   (ii) having an amino acid sequence which is at least 80% identical to the sequence of SEQ ID No. 1 or 2;

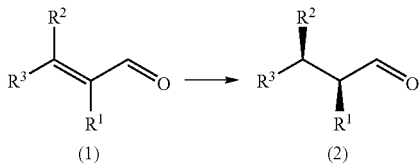

wherein
$R_1$ and $R_2$
   are, independently of one another, H or $C_1$-$C_4$-alkyl; and
$R_3$ is H or $C_1$-$C_6$-alkyl or alkenyl, wherein said alkyl or alkenyl is branched or unbranched,
   wherein said α,β-unsaturated aldehyde of formula (1) is reduced to the optically active aldehyde of formula (2) and/or the corresponding alcohol of formula (2).

2. The process of claim 1, wherein said reduction is carried out in the presence of a cofactor.

3. The process of claim 2, wherein said cofactor is NADPH.

4. The process of claim 2, wherein used cofactor is regenerated enzymatically.

5. The process of claim 4, wherein used cofactor is regenerated with glucose dehydrogenase.

6. The process of claim 1, wherein said reduction is carried out in an aqueous system.

7. The process of claim 1, wherein said enoate reductase is in an immobilized form.

8. The process of claim 1, wherein said α,β-unsaturated aldehyde of formula (1) is citral, said optically active aldehyde of formula (2) is (R)-(+)-citronellal and/or said corresponding alcohol of formula (2) is (R)-(+)-β-citronellol.

9. A process for preparing a compound selected from the group consisting of (R)-(+)-citronellal, (R)-(+)-β-citronellol, nerol, geraniol, a combinations thereof comprising reducing citral in the presence of an enoate reductase
   (i) having the amino acid sequence SEQ ID No. 1 or 2; or
   (ii) having an amino acid sequence which is at least 80% identical to the sequence of SEQ ID No. 1 or 2;
   to form a compound selected from the group consisting of (R)-(+)-citronellal, (R)-(+)-β-citronellol, nerol, geraniol, and combinations thereof.

* * * * *